United States Patent
Patruno et al.

(10) Patent No.: US 10,368,833 B2
(45) Date of Patent: Aug. 6, 2019

(54) METHOD AND SYSTEM FOR FETAL VISUALIZATION BY COMPUTING AND DISPLAYING AN ULTRASOUND MEASUREMENT AND GRAPHICAL MODEL

(71) Applicant: General Electric Company, Schenectady, NY (US)

(72) Inventors: Francesca Patruno, Glenview, IL (US); Simon Scharinger, Upper Austria (AT); Klaus Pintoffl, Styria (AT); Walter Duda, Jr., Upper Austria (AT); Karl-Heinz Lumpi, Upper Austria (AT); Lucienne van der Veen, Lower Austria (AT)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 945 days.

(21) Appl. No.: 14/484,503

(22) Filed: Sep. 12, 2014

(65) Prior Publication Data
US 2016/0074006 A1 Mar. 17, 2016

(51) Int. Cl.
*A61B 8/14* (2006.01)
*A61B 8/08* (2006.01)
(Continued)

(52) U.S. Cl.
CPC .............. *A61B 8/0866* (2013.01); *A61B 8/14* (2013.01); *A61B 8/463* (2013.01); *A61B 8/5207* (2013.01);
(Continued)

(58) Field of Classification Search
CPC .... A61B 8/00; A61B 8/13; A61B 8/14; A61B 8/0866; A61B 8/5223
See application file for complete search history.

(56) References Cited

U.S. PATENT DOCUMENTS

| 5,222,485 A | 6/1993 | Jerath |
| 5,876,357 A | 3/1999 | Tomer |

(Continued)

FOREIGN PATENT DOCUMENTS

| WO | 2002098271 A2 | 12/2002 |
| WO | 2005077261 A1 | 8/2005 |

(Continued)

OTHER PUBLICATIONS

International Search Report and Written Opinion from corresponding PCT application No. PCT/US2015/047673 dated Nov. 26, 2015; 15 pages.

(Continued)

*Primary Examiner* — Tse W Chen
*Assistant Examiner* — Jason M Ip
(74) *Attorney, Agent, or Firm* — McAndrews, Held & Malloy, Ltd.; Jacob Groethe; David Bates

(57) ABSTRACT

Various embodiments include a system and method that provide fetal visualization. The method can include acquiring, by an ultrasound system, ultrasound data for a region of interest. The method may include computing, by a processor of the ultrasound system, a fetal measurement based on the acquired ultrasound data. The method can include generating, by the processor, a graphical model based on one or more of the fetal measurement and the acquired ultrasound data. The method may include displaying, at a display system, the computed fetal measurement and the generated graphical model.

20 Claims, 5 Drawing Sheets

(51) Int. Cl.
*A61B 8/00* (2006.01)
*G06T 7/12* (2017.01)
*G06T 7/13* (2017.01)
*G06T 7/181* (2017.01)

(52) U.S. Cl.
CPC .............. *A61B 8/5223* (2013.01); *G06T 7/12* (2017.01); *G06T 7/13* (2017.01); *G06T 7/181* (2017.01); *G06T 2207/10132* (2013.01); *G06T 2207/20016* (2013.01); *G06T 2207/30008* (2013.01); *G06T 2207/30044* (2013.01); *G06T 2207/30101* (2013.01)

(56) References Cited

U.S. PATENT DOCUMENTS

| | | | |
|---|---|---|---|
| 6,200,279 | B1 | 3/2001 | Paltieli |
| 6,464,639 | B1* | 10/2002 | Kim ..................... G09B 23/30 128/916 |
| 6,591,004 | B1* | 7/2003 | VanEssen .............. G06T 17/00 128/922 |
| 6,669,653 | B2 | 12/2003 | Paltieli |
| 7,207,941 | B2 | 4/2007 | Sharf |
| 7,850,625 | B2 | 12/2010 | Paltieli |
| 8,292,831 | B2 | 10/2012 | Fausett et al. |
| 8,840,557 | B2 | 9/2014 | Casciaro |
| 8,891,881 | B2 | 11/2014 | Gupta |
| 2003/0114779 | A1 | 6/2003 | Paltieli |
| 2004/0236193 | A1 | 11/2004 | Sharf |
| 2006/0015036 | A1 | 1/2006 | Paltieli |
| 2008/0167553 | A1 | 7/2008 | Paltieli |
| 2008/0167581 | A1 | 7/2008 | Paltieli |
| 2008/0249755 | A1* | 10/2008 | Tek .................... A61B 5/02014 703/11 |
| 2009/0093716 | A1 | 4/2009 | Deischinger et al. |
| 2011/0112403 | A1 | 5/2011 | Machtey |
| 2011/0257529 | A1 | 10/2011 | Casciaro |
| 2012/0249764 | A1 | 10/2012 | Kuon et al. |
| 2013/0060119 | A1 | 3/2013 | Weeks et al. |
| 2013/0190600 | A1 | 7/2013 | Gupta |
| 2013/0218015 | A1 | 8/2013 | Machtey et al. |
| 2016/0045152 | A1 | 2/2016 | Singhal et al. |
| 2016/0074006 | A1 | 3/2016 | Patruno |
| 2017/0206659 | A1 | 7/2017 | Perrey |

FOREIGN PATENT DOCUMENTS

| | | |
|---|---|---|
| WO | 2005096707 | 10/2005 |
| WO | 2010057665 A1 | 5/2010 |
| WO | 2013103818 | 7/2013 |

OTHER PUBLICATIONS

A.M. Duckelmann et al., "Measurement of fetal head descent using the 'angle of progression' on transperineal ultrasound imaging is reliable regardless of fetal head station or ultrasound expertise". Ultrasound in Obstetrics and Gynecology, vol. 35, No. 2, Feb. 1, 2010, pp. 216-222.

A.F. Barbera et al., "A new method to assess fetal head descent in labor with transperineal ultrasound", Ultrasound in Obstetrics and Gynecology, vol. 33, No. 3, Mar. 1, 2009, pp. 313-319.

Foroughi P et al., "Ultrasound Bone Segmentation Using Dynamic Programming", Ultrasonics Symposium, 2007, IEEE, IEEE, Piscataway, NJ, USA, Oct. 1, 2007, pp. 2523-2526.

Office Action for Chinese Patent Application No. 201580048924.1, dated May 10, 2019, 6 pages.

Kalache et al., "Transperineal ultrasound imaging in prolonged second stage of labor with occipitoanterior presenting fetuses: how well does the 'angle of progression' predict the mode of delivery?," Ultrasound Obstet Gynecol 2009, vol. 33, pp. 326-330.

Duckelman et al., "Measurement of fetal head descent using the 'angle of progression' on transperineal ultrasound imaging is reliable regardless of fetal head station or ultrasound expertise," Ultrasound Obstet Gynecol 2010, NCBI, vol. 35, pp. 216-222.

Bamberg C et al., "Angle of progression measurements of fetal head at term: a systematic comparison between open magnetic resonance imaging and transperineal ultrasound," American Journal of Obstetrics, vol. 206, Issue 2, Feb. 2012, pp. 161-162.

Casciaro et al., "Automatic Evaluation of Progression Angle and Fetal Head Station through Intrapartum Echographic Monitoring," Computational and Mathematical Methods in Medicine, Hindawi Publishing Corporation, Aug. 2013, pp. 1-8.

Barbera, Antonio F., "The Angle of Progression: An Objective Assessment of Fetal Head Descent in the Birth Canal," Intrapartum Ultrasonography for Labor Management (2012), pp. 87-100.

Khalil et al., "Assessment of the progress of labor by the use of intrapartum ultrasound," Alexandria Journal of Medicine, (2012), 48: pp. 295-301.

Molina et al., "What is the most reliable ultrasound parameter for assessment for fetal head descent?" Ultrasound Obstet Gynecol, (2010), 36: pp. 493-499.

Fouche et al., "Ultrasound in monitoring of the second stage of labour,"+Gynecologie Obstetrique & Fertillite 40 (2012), pp. 658-665.

* cited by examiner

METHOD AND SYSTEM FOR FETAL VISUALIZATION BY COMPUTING AND DISPLAYING AN ULTRASOUND MEASUREMENT AND GRAPHICAL MODEL

CROSS-REFERENCE TO RELATED APPLICATIONS/INCORPORATION BY REFERENCE

[Not Applicable]

FIELD OF THE INVENTION

Certain embodiments of the invention relate to ultrasound imaging. More specifically, certain embodiments of the invention relate to a method and system for fetal visualization, such as labor progress, based on a graphical model and ultrasound measurement.

BACKGROUND OF THE INVENTION

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image.

Ultrasound imaging may be helpful in evaluating the progression of labor and/or other fetal measurements by allowing examination of cervical dilation, fetal presentation, position, and descent. A prolonged second stage of labor is a type of dystocia, whereby the fetus has not been delivered within three hours in nulliparous women or two hours in multiparous women, after the cervix has become fully dilated. Women undergoing a prolonged second stage of labor typically need intervention, which involves instrumental delivery (using obstetric forceps or ventouse) or Cesarean section or failed instrumental delivery followed by Cesarean section.

In recent years, the rate of Cesarean section has increased dramatically. The failure to progress and fetal distress are the two most common indications for performing surgical deliveries or Cesarean section. Cesarean sections are associated with the risk of maternal morbidities such as bladder trauma and hematoma and unnecessary Cesarean sections are best avoided.

Currently, digital examination of fetal descent using transvaginal imaging is considered the 'gold standard' for evaluating fetal head station, but this method is subjective and inaccurate with high interobserver variability. Recent studies have shown that transperineal ultrasound imaging might allow objective quantification of the level of fetal head descent in the birth canal. Multiple measurements have been proposed including the fetal head-perineum distance and measuring the 'angle of progression' (AOP) to evaluate the labor progress. With regard to AOP, it has been shown that the greater the AOP in the second stage of labor, the greater the probability of successful assisted or spontaneous delivery. Studies with fetuses in the direct occipitoanterior position have shown that the AOP correlates well with the decision to opt for spontaneous vaginal or instrumental delivery or Cesarean section. There is growing evidence suggesting that, AOP may constitute a suitable, objective tool to evaluate progress of labor.

Earlier efforts at improving robustness and accuracy of clinical workflow in the labor room combine position tracking technology with advanced ultrasound imaging to objectively determine fetal head station. For example, LABORPRO, which was developed by TRIG MEDICAL, maps the maternal pelvis by manually marking points on the pelvis or using a position sensor. This is followed by marking known fetal head landmarks on the ultrasound image. The two markings enable LABORPRO to determine the spatial position of the fetal head in relation to the pelvic bone. However, the system in LABORPRO does not work fully automatically and requires manual interaction. Existing systems also do not display labor progress or other fetal measurement information in a manner suitable for understandability by non-medical persons.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY OF THE INVENTION

A system and/or method is provided for fetal visualization by computing and displaying an ultrasound measurement and graphical model, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION OF THE INVENTION

Figure 1:
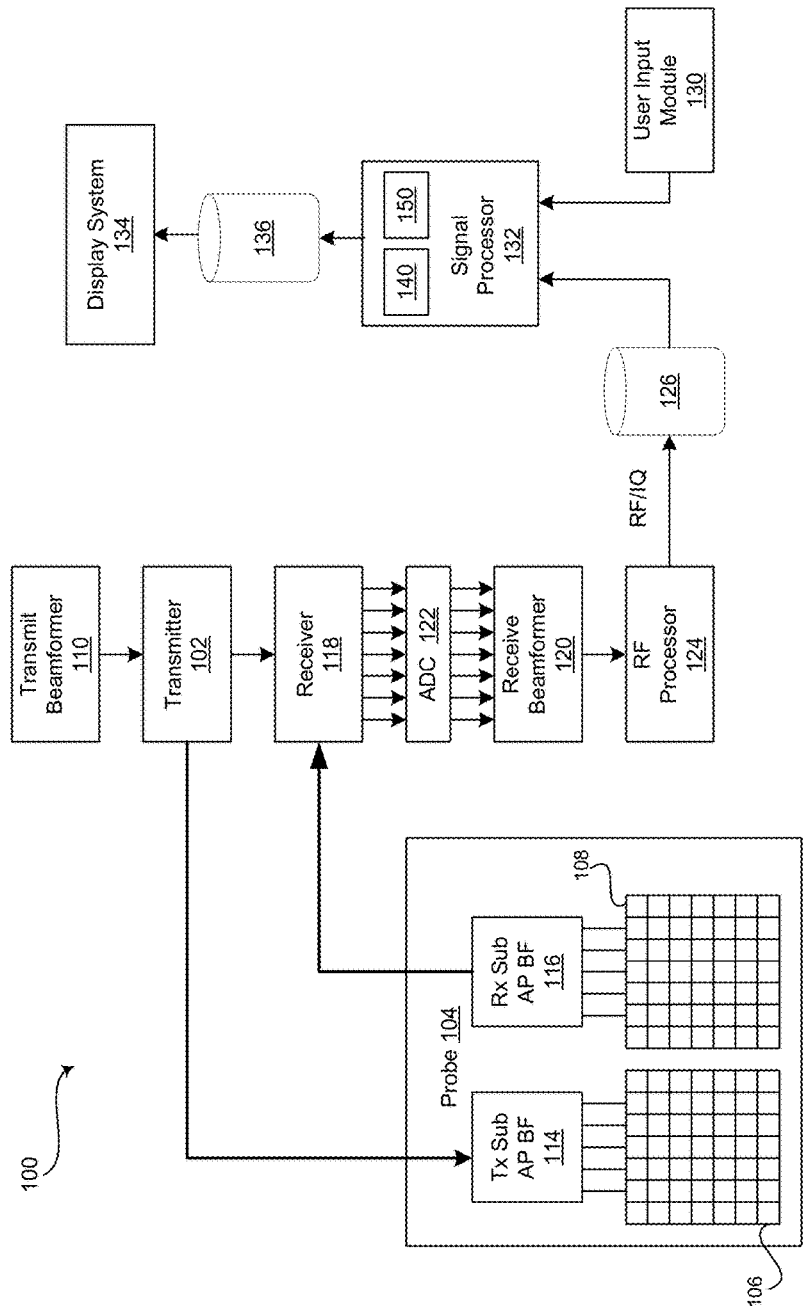
FIG. 1 is a block diagram of an exemplary ultrasound system that is operable to provide fetal visualization based on a graphical model and measurement, in accordance with an embodiment of the invention.

Certain embodiments of the invention may be found in a method and system for providing fetal visualization by computing and displaying an ultrasound measurement and graphical model.

Various embodiments include a system 100 and method 300 that provide fetal visualization. The method 300 can include acquiring 302, by an ultrasound system 100, ultrasound data for a region of interest. The method 300 may include computing 304, by a processor 132, 140 of the ultrasound system 100, a fetal measurement based on the acquired ultrasound data. The method 300 can include generating 306, by the processor 132, 150, a graphical model based on the acquired ultrasound data. The method 300 may include displaying 308, at a display system 134, the computed fetal measurement 220 and the generated graphical model 210.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an exemplary embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

In addition, as used herein, the phrase "pixel" also includes embodiments of the present invention where the data is represented by a "voxel". Thus, both the terms "pixel" and "voxel" may be used interchangeably throughout this document.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or submodes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the invention, such as single or multi-core: CPU, Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system that is operable to provide fetal visualization based on a graphical model and measurement, in accordance with an embodiment of the invention. Referring to FIG. 1, there is shown an ultrasound system 100. The ultrasound system 100 comprises a transmitter 102, an ultrasound probe 104, a transmit beamformer 110, a receiver 118, a receive beamformer 120, a RF processor 124, a RF/IQ buffer 126, a user input module 130, a signal processor 132, an image buffer 136, and a display system 134.

The transmitter 102 may comprise suitable logic, circuitry, interfaces and/or code that may be operable to drive an ultrasound probe 104. The ultrasound probe 104 may comprise a two dimensional (2D) or three dimensional (3D) array of piezoelectric elements. The ultrasound probe 104 may comprise a group of transmit transducer elements 106 and a group of receive transducer elements 108, that normally constitute the same elements.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive and demodulate the signals from the receive sub-aperture beamformer 116. The demodulated analog signals may be communicated to one or more of the plurality of A/D converters 122.

The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120.

Notwithstanding, the invention is not limited in this regard. Accordingly, in some embodiments of the invention, the plurality of A/D converters 122 may be integrated within the receiver 118.

The receive beamformer 120 may comprise suitable logic, circuitry, interfaces and/or code that may be operable to perform digital beamforming processing to, for example, sum the delayed channel signals received from the plurality of A/D converters 122 and output a beam summed signal. The resulting processed information may be converted back to corresponding RF signals. The corresponding output RF signals that are output from the receive beamformer 120 may be communicated to the RF processor 124. In accordance with some embodiments of the invention, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment of the invention, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The user input module 130 may be utilized to input patient data, surgical instrument data, scan parameters, settings, configuration parameters, change scan mode, and the like. In an exemplary embodiment of the invention, the user input module 130 may be operable to configure, manage and/or control operation of one or more components and/or modules in the ultrasound system 100. In this regard, the user input module 130 may be operable to configure, manage and/or control operation of transmitter 102, the ultrasound probe 104, the transmit beamformer 110, the receiver 118, the receive beamformer 120, the RF processor 124, the RF/IQ buffer 126, the user input module 130, the signal processor 132, the image buffer 136, and/or the display system 134.

The signal processor 132 may comprise suitable logic, circuitry, interfaces and/or code that may be operable to process ultrasound scan data (i.e., RF signal data or IQ data pairs) for generating an ultrasound image for presentation on a display system 134. The signal processor 132 is operable to perform one or more processing operations according to a plurality of selectable ultrasound modalities on the acquired ultrasound scan data. In an exemplary embodiment of the invention, the signal processor 132 may be operable to perform compounding, motion tracking, and/or speckle tracking. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation.

The ultrasound system 100 may be operable to continuously acquire ultrasound scan data at a frame rate that is suitable for the imaging situation in question. Typical frame rates range from 20-70 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several seconds' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a fetal measurement processing module 140 that comprises suitable logic, circuitry, interfaces and/or code that may be operable to compute a measurement corresponding with a fetus. For example, the measurement may relate to a progress of delivery, biparietal diameter (BPD), head circumference, abdominal circumference, humerus length, femur length, or any suitable fetal measurement. Examples of progress of delivery measurements include a fetal head-perineum distance measurement, an "angle of progression" (AOP) measurement, a distance of progression measurement, a head direction measurement, a fetal head rotation measurement, or any suitable measurement related to evaluating labor progress. The measurement may be computed automatically based on the ultrasound scan data acquired by the ultrasound probe 104 and/or manually based on the ultrasound scan data and user input received from the user input module 130, for example. The fetal measurement is displayed for interpretation at display system 134.

The signal processor 132 may include a graphical model generation module 150 that comprises suitable logic, circuitry, interfaces and/or code that may be operable to process ultrasound scan data to form a graphical model that may be provided to the image buffer 136 and/or the display system 134. The graphical model may be a three-dimensional (3D) graphical model, for example. For example, the graphical model generation module 150 may access standard or generic models of structures such as a fetus and a womb, among other things. The standard or generic structural models may be combined to form the graphical model based on the fetal measurement and/or ultrasound scan data. As an example, a standard or generic fetus model can be positioned within a standard or generic womb model based on, for example, an AOP measurement to generate the graphical model illustrating labor progression. In a representative embodiment, a representation of the graphical model is updated in real time on the display system 134. In various embodiments, the graphical model may be displayed in parallel with a live ultrasound image. For example, the representation of the graphical model may be displayed side-by-side with the live ultrasound image or in a top/bottom orientation with the live ultrasound image.

Figure 2:
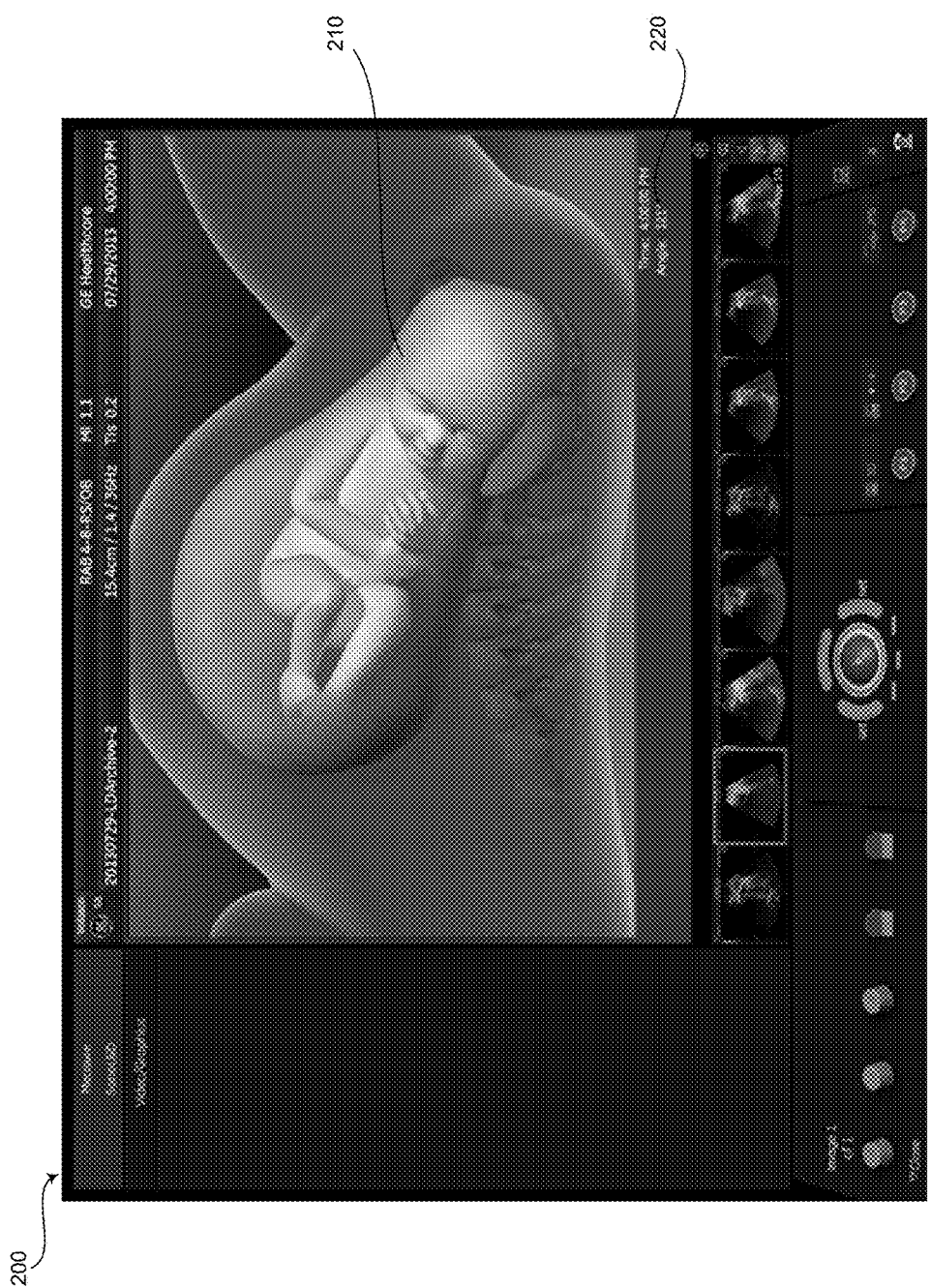
FIG. 2 illustrates an exemplary display of a graphical model and ultrasound measurement, in accordance with an embodiment of the invention.

FIG. 2 illustrates an exemplary display 200 of a graphical model 210 and ultrasound measurement 220, in accordance with an embodiment of the invention. Referring to FIG. 2, the display 200 may be presented on a display device such as the display system 134 as shown in FIG. 1. The display 200 comprises a graphical model 210 and a measurement 220. The graphical model 210 may be the graphical model formed by the graphical model generation module 150 as shown in FIG. 1. The measurement 220 may be the measurement computed by the fetal measurement processing module 140 as shown in FIG. 1. Although the displayed measurement 220 is an AOP measurement, additional and/or alternative measurements may be displayed. For example, the measurement 220 may also be a biparietal diameter (BPD) measurement, head circumference measurement, abdominal circumference measurement, humerus length measurement, femur length measurement, fetal head-perineum distance measurement, a distance of progression measurement, a head direction measurement, a fetal head rotation measurement, and/or any suitable measurement or combination of measurements related to evaluating a fetus and/or labor progress. Further, although the displayed measurement 220 is shown in a lower right corner of the graphical model, the measurement 220 can additionally and/or alternatively be positioned anywhere on the display 200, including being overlaid on the graphical model 210 such that the overlaid information identifies the measurement 220 on the graphical model 210. For example, a femur length measurement may identify the femur in the graphical model 210 and illustrate a start point and end point of the measurement along with the measurement itself such that medical and/or non-medical personnel viewing the display 200 may readily understand the measurement information 220 in the context of the graphical model 210.

Figure 3:
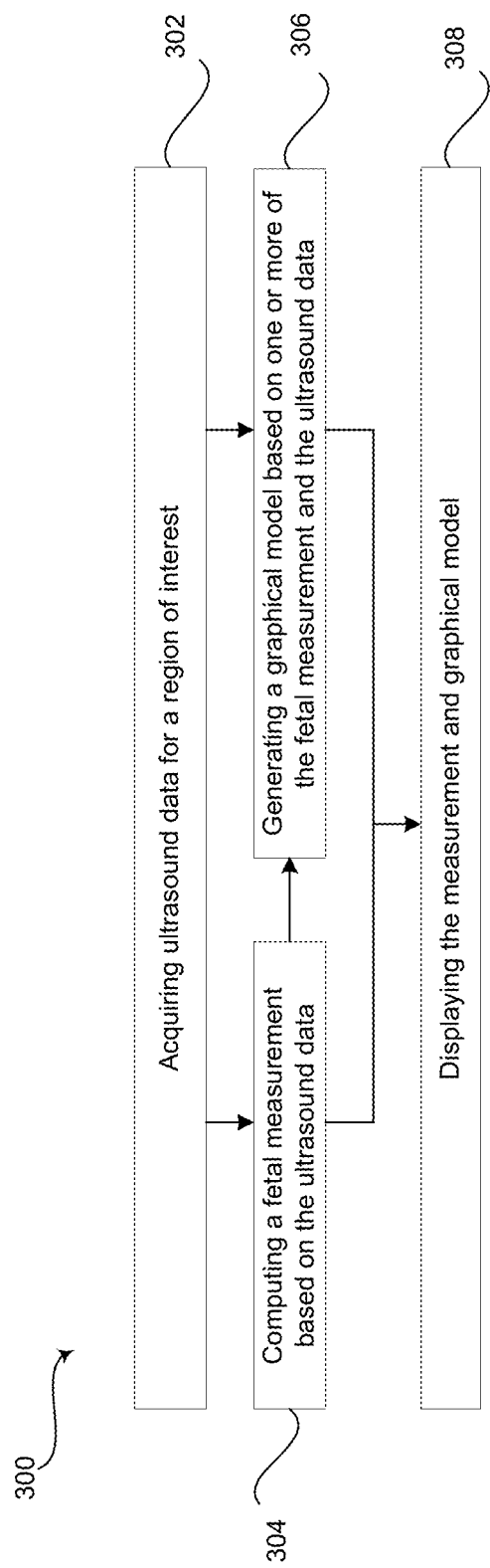
FIG. 3 is a flow chart illustrating exemplary steps that may be utilized for providing fetal visualization based on a graphical model and measurement, in accordance with an embodiment of the invention.

FIG. 3 is a flow chart illustrating exemplary steps that may be utilized for providing fetal visualization based on a graphical model and measurement, in accordance with an embodiment of the invention. The technical effect of the method 300 is the computation and display of a fetal measurement 220 (shown in FIG. 2) and a representation of a graphical model 210 on a display device such as the display system 134 (shown in FIG. 1). Referring to FIG. 3, there is shown a flow chart 300 comprising exemplary steps 302 through 308. Certain embodiments of the present invention may omit one or more of the steps, and/or perform the steps in a different order than the order listed, and/or combine certain of the steps discussed below. For example, some steps may not be performed in certain embodiments of the present invention. As a further example, certain steps may be performed in a different temporal order, including simultaneously, than listed below.

In step 302, an ultrasound system 100 acquires ultrasound data, for example, as described above with regard to FIG. 1. The ultrasound system 100 may be performing transperineal ultrasound imaging to acquire the data, for example. The ultrasound data may be representative of, for example, a fetus in the direct occipitoanterior position. In step 304, the fetal measurement processing module 140 of the signal processor 132 may compute a measurement related to a fetus based on the ultrasound data acquired at step 302. The fetal measurement processing module 140 may compute the measurement automatically or based in part on user input from a user input module 130. The measurement may be a biparietal diameter (BPD) measurement, a head circumference measurement, an abdominal circumference measurement, a humerus length measurement, a femur length measurement, a fetal head-perineum distance measurement, an AOP measurement (as described below with reference to FIG. 4, for example), a distance of progression measurement, a head direction measurement, a fetal head rotation measurement, or any suitable measurement related to a fetus and/or evaluating labor progress.

In step 306, graphical model generation module 150 of the signal processor 132 may generate a graphical model based on the fetal measurement computed at step 304 and/or the ultrasound data acquired at step 302. The graphical model may be a three-dimensional (3D) graphical model of a standard or generic fetus model in a standard or generic womb model, where the fetus model is positioned with respect to the womb model based on an AOP measurement, for example. In step 308, the display system 134 of the ultrasound system 100 may display the measurement computed at step 304 and the graphical model generated at step 306 as illustrated in FIG. 2, for example.

Figure 4:
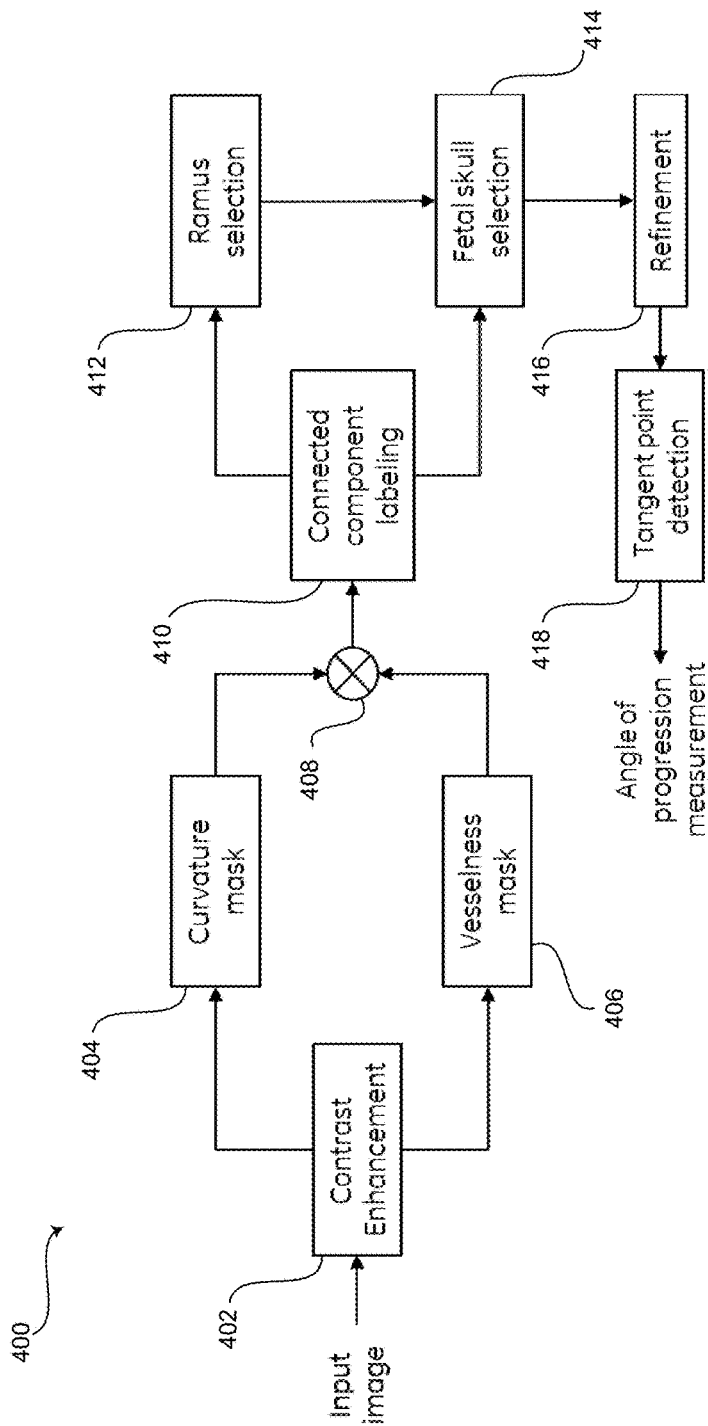
FIG. 4 is a flow chart illustrating exemplary steps that may be utilized for performing an angle of progression measurement, in accordance with an embodiment of the invention.

FIG. 4 is a flow chart illustrating exemplary steps that may be utilized for performing an "angle of progression" (AOP) measurement based on ultrasound data, in accordance with an embodiment of the invention. The technical effect of the method 400 is the computation of the AOP measurement by a signal processor 132, 140 (shown in FIG. 1). Referring to FIG. 4, there is shown a flow chart 400 comprising exemplary steps 402 through 418. Certain embodiments of the present invention may omit one or more of the steps, and/or perform the steps in a different order than the order listed, and/or combine certain of the steps discussed below. For example, some steps may not be performed in certain embodiments of the present invention. As a further example, certain steps may be performed in a different temporal order, including simultaneously, than listed below.

The method 400 comprises of automated detection of pubic ramus and fetal skull contour followed by finding the point where the line from the inferior apex of the pubic ramus (right end point) intersects the fetal skull contour tangentially. Finally the AOP is measured as the angle between the line drawn along the pubic ramus and the line extending from the right end point of the pubic ramus to the tangent point on fetal skull contour.

More specifically, in step 402, contrast enhancement is applied to acquired ultrasound scan data. While the tissue lining the pubic ramus and fetal skull is a continuous and coherent entity, they often appear disjointed in ultrasound images owing to several factors some of which could be related to tissue alignment (tissue scatters ultrasound beam away from the probe) and tissue occlusion. As such, a filter smoothens across these spatial discontinuities while preserving the contrast between the tissue and its surrounding background. For example, the filter may be transformed into an anisotropic diffusion filter, which is further formulated into a level set function. The ultrasound scan data is interpreted as a collection of iso-intensity contours and, under a curvature-driven factor, smoothing takes place inside a region, but not across region boundaries resulting in sharp boundaries being preserved while speckles are smoothened.

The contrast enhancement applied in step 402 improves the tissue signature in the pubic ramus and fetal skull. In steps 404, 406, and 408, the enhanced image is transformed into a binary representation of the image pixels corresponding to the pubic ramus and fetal skull. In addition to the pubic ramus and fetal skull tissue, other structures/noise also get highlighted in the process of contrast enhancement and selecting the desired anatomical structures becomes difficult.

In step 404, a curvature mask is applied to the contrast enhanced image. As previously mentioned the pubic ramus and fetal skull has a ridge like appearance and therefore a high curvature. The local (pixel-wise) curvature can be estimated from the intensity image based on:

$$I_c = div\left(\frac{\nabla I}{\|\nabla I\|}\right)$$

Where, I is the input image (contrast enhanced image) and Ic is the image obtained after curvature transform. If a point belongs to pubic ramus or fetal skull cranium bone, then it will have intensity higher compared to its neighbor, such that the vector field points inward towards the region. Therefore, the divergence of the vector field in that region would have a negative value, as the region is a sink. If the region does not belong to bone, ideally the divergence should be positive and the region is called a source. As a result, the image Ic is set less than T(−0.3) as the region with negative value represents the required anatomical bone structures. A higher threshold value reduces the filter response which results in missing or partial extraction of required components. A lower threshold value results in large number of noisy components which make the down selection of required structures difficult.

$$I_{mc} = \begin{cases} 1, & \text{if } I_c < T \\ 0, & \text{else} \end{cases}$$

In step 406, a vesselness mask is applied to the contrast enhanced image. The vesselness mask computes the likelihood of the contrast enhanced image to contain vessel/ridge like structures. Since the pubic ramus and fetal skull resembles a ridge, the vesselness mask is well suited for segmenting these anatomical features. In the first step the contrast enhanced image from step 402 is convolved with a series of Gaussian second derivative filters and the responses at each image pixel are stacked in a [2×2] matrix to obtain the Hessian.

$$D_{xx} = H_{xx} * I,$$
$$D_{yy} = H_{yy} * I,$$
$$D_{xy} = H_{xy} * I,$$
$$D = \begin{bmatrix} D_{xx} & D_{xy} \\ D_{yx} & D_{yy} \end{bmatrix}$$

where, I is the input image, $H_{xx}$, $H_{yy}$, and $H_{xy}$ are the second derivative Gaussian filters, * is the convolution operator, and D is the Hessian matrix formed by stacking the filter outputs $D_{xx}$, $D_{yy}$, and $D_{xy}$, at each image pixel. The ratio of eigenvalues of the matrix D(=$1_1$; $1_2$) is a measure of the isotropy of the underlying structure. A small ratio is indicative of a ridge like feature that possesses a definitive orientation and therefore exhibits strong anisotropy. This anisotropy can be emphasized by embedding the ratio of the eigenvalues into a functional form as expressed below:

$$I_f = \exp\left(\frac{-\left(\frac{\lambda_2}{\lambda_1}\right)^2}{\beta}\right)\left(1 - \exp\left(\frac{-(\lambda_1^2 + \lambda_2^2)}{c}\right)\right)$$

where, $I_f$ is the filtered output, b(=1) and c(=450) are constants. The filtered output varies in the range [0, 1] with values near one indicating a strong presence of a ridge-like structure. Since the anatomical structure might manifest itself at different scales, the algorithm is repeated at multiple scales (e.g., 5 scales) and the maximum output from all the scales at each pixel is stored as the final output. The maximum scale value (e.g., 5) is determined on the basis of the width range of the vessels of interest (pubic ramus and fetal skull in this case) at a particular resolution. Selecting a higher maximum scale value does not affect the output significantly, if the maximum width among the objects of interest is below the selected maximum scale. However, a higher maximum scale value results in more computation and reduces the execution speed. On the other hand, a lower maximum scale value can affect the output as vessels with width larger than the maximum scale are not able to reach the optimal response. The output of the vesselness mask is binarized by selecting a threshold to yield the binary image $I_{fm}$. The threshold of 0.5 may be selected to maximize the response of the mask while reducing the number of noisy components. A higher threshold value may reduce the mask response which results in missing or partial extraction of required vessels. A lower threshold value results in large number of noisy components which makes the down selection of required vessels difficult.

In step 408, the output of the curvature mask applied at step 404 and the output of the vesselness mask applied at step 406 are combined. Quite often, the pubic ramus and fetal skull do not appear as distinct entities in the output of the vesselness mask, but are connected to neighboring structures or noise. The output of the curvature mask on the other hand gives them a distinct appearance; however, it is accompanied by noise artifacts. In order to prune and remove noise artifacts, the outputs of the two masks may be combined by a pixel-to-pixel AND operation:

$$I_{comb} = I_{fm} \text{ AND } I_{mc}$$

In step 410, the connected components in the output of the combined masks $I_{comb}$ is annotated with labels. Each distinct object is given a unique identifier or label, while the background is set to zero. An object or connected component is usually defined as a set of connected, nonzero pixels, where two pixels being connected means that it is possible to construct a path including only non-zero pixels between them. Steps along the path may be defined by an 8-connected neighborhood function. In an embodiment, in order to remove noise components, all connected components (objects) that have fewer than 50 pixels, for example, may be removed.

In step 412, the pubic ramus is automatically selected from several objects of the outputted connected component labeled image. The choice may be made on the basis of a cost function premised on pubic ramus anatomy, its size, location, and presentation in the imaging scan plane. The location of the pubic ramus within the symphyseal capsular tissue may be determined by a heuristic approach that identifies the objects in the top left half of the image. The pubic ramus appears as an object of high intensity and is typically brighter than other objects in the vicinity. Another potential discriminator in the down selection of pubic ramus component is the concavity of the component with respect to the lateral resolution.

While in reality pubic ramus and fetal skull is a continuous and coherent entity, even in the contrast enhanced image, they could appear discontinuous. As such, disjointed components in local neighborhood of a candidate component are combined based on similarity of curvature. A disjointed component with similar curvature results in lower fitting error.

The final selection of the component representing the pubic ramus is based on a cost function that uses the length, intensity, vesselness, and concavity of the component. The selection is described as:

$$R_c = \underset{i \in 1,2,\ldots,N_r}{\arg\max} \; (C_i + mV_i + mI_i + l_i)$$

where, $C_i$, $mV_i$, $mI_i$, $I_i$ are the measure of concavity, mean vesselness, mean intensity, and length of the ith component, respectively, $N_r$ is the total number of components after combining disjointed components located in the top left half of the imaging scan plane, and $R_c$ is the selected pubic ramus component.

In step 414, the component representing the leading edge of the fetal skull is automatically selected from the several objects of the outputted connected component labeled image at step 410 in view of the pubic ramus selection at step 412. The component representing the leading edge of the fetal skull is selected based on a cost function similar to pubic ramus selection. The cost function is premised on the fetal skull anatomy, its location, and presentation. The fetal skull is assumed to be below the pubic ramus. The fetal skull appears as an object of high intensity and is typically brighter than other objects in the vicinity. Another potential discriminator in the down selection of the fetal skull component is the concavity of the component with respect to the lateral direction. Selection process similar to pubic ramus selection is followed in down selecting the fetal skull component. Disjointed components are combined and selection is made using the cost function:

$$H_c = \underset{\substack{i \in 1,2, \ldots, N_h, \\ hm \text{ below } H_c}}{\arg\max} \left( C_i + mV_i + ml_i + l_i \right)$$

where, $N_h$ is the total number of components that lie within the search constraint and is the selected fetal skull component.

In step 416, the image outputted after the fetal skull selection at step 414 is refined prior to detecting a tangent point on the fetal skull in the image at step 418 as described below.

In step 418, a tangent point on the fetal skull is detected. The tangent point may be the point where the line extending from the inferior apex of the public ramus (right end point) intersects the fetal skull contour tangentially. The fetal skull contour is modeled by a polynomial regression equation, represented by:

$$P = p_n r^n + p_{n-1} x^{n-1} + \ldots + p_1 x + p_0$$

where, n=2, 3, representing quadratic and cubic regression models, respectively. For each point lying on the fetal skull contour, two slopes $s_1$ and $s_2$ are computed. $s_1$ is the slope of a tangent line to the curve P at the candidate point and $s_2$ is the slope of the line extending from the inferior apex of the pubic ramus to the candidate point. The best fitted model and the tangent point is estimated by comparing the two slopes. The point where the two slopes $S_1$ and $s_2$ have minimum absolute difference is expressed as the tangent point. The computation is described as:

$$(x_t, y_t) = \underset{(x_t, y_t) \in H_c, n \in \{2,3\}}{\arg\min} \left\| (np_n x_i^{n-1} + (n-1) p_{n-1} x_i^{n-2} \ldots + p_1) - \left( \frac{(y_i - y_2)}{(x_i - x_2)} \right) \right\|_1$$

where, $H_c$ is the fetal skull contour, $(x_2, y_2)$ is the right pubic ramus end point, and $(x_t, y_2)$ is the computed tangent point. Alternatively, in certain embodiments, the tangent point may be manually selected based on a user input at user input module 130, for example.

Figure 5:
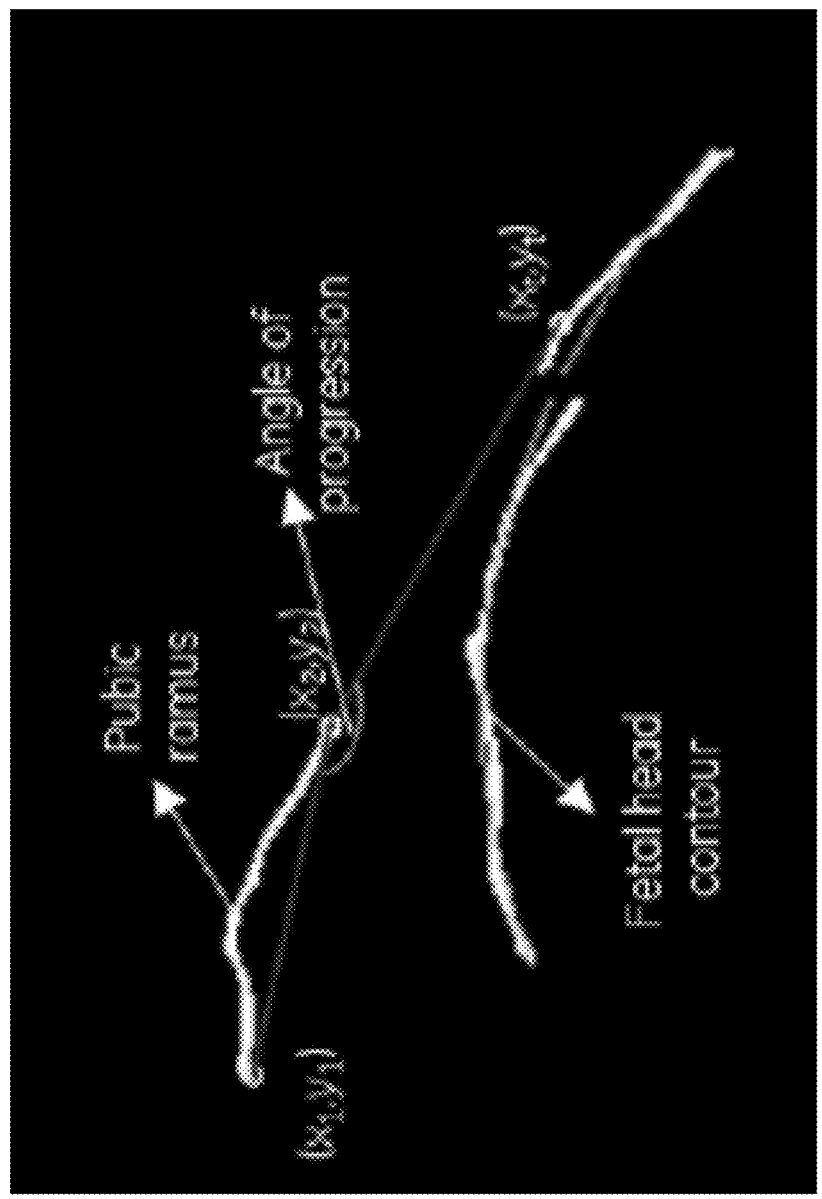
FIG. 5 is an image illustrating an exemplary angle of progression measurement, in accordance with an embodiment of the invention.

The AOP measurement is the angle between the line drawn along the pubic rams and the line extending from the inferior apex (right end point) of the pubic ramus (right end point) tangentially to the fetal skull contour. FIG. 5 illustrates an example of the AOP. In an exemplary embodiment, the AOP measurement computed based on method 400 may be step 304 of method 300. The AOP measurement 220 may then be displayed in step 308 as illustrated in FIG. 2, or example.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the invention may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for providing fetal visualization by computing and displaying an ultrasound measurement and a graphical model.

Accordingly, the present invention may be realized in hardware, software, or a combination of hardware and software. The present invention may be realized in a centralized fashion in at least one computer system, or in a distributed fashion where different elements are spread across several interconnected computer systems. Any kind of computer system or other apparatus adapted for carrying out the methods described herein is suited.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method for fetal visualization, the method comprising:
   acquiring, by an ultrasound system, ultrasound data for a region of interest;
   computing, by a processor of the ultrasound system, one or more fetal measurements based on the acquired ultrasound data, wherein the one or more fetal measurements comprise an angle of progression measurement;

generating, by the processor, a graphical model based at least in part on the angle of progression measurement; and displaying, at a display system, the one or more computed fetal measurements and the generated graphical model.

2. The method according to claim 1, wherein the ultrasound data is acquired by transperineal ultrasound imaging.

3. The method according to claim 1, wherein the graphical model is a three-dimensional graphical model comprising a standard or generic fetus model positioned within a standard or generic womb model based on the angle of progression measurement.

4. The method according to claim 1, comprising:
applying contrast enhancement to the acquired ultrasound data to generate a contrast enhanced image; and
generating a binary representation of image pixels corresponding to a pubic ramus and a fetal skull in the contrast enhanced image by:
applying a curvature mask to the contrast enhanced image to generate a curvature mask output image,
applying a vesselness mask to the contrast enhanced image to generate a vesselness mask output image, and
combining the curvature mask output image and the vesselness mask output image.

5. The method according to claim 1, comprising automatically selecting a pubic ramus and a fetal skull contour in the acquired ultrasound data.

6. The method according to claim 5, comprising detecting a tangent point where a line extending from an inferior apex of the pubic ramus intersects the fetal skull contour tangentially.

7. The method according to claim 6, wherein the angle of progression measurement is computed as the angle between a line drawn along the pubic ramus and the line extending from the inferior apex of the pubic ramus to the tangent point.

8. A system for fetal visualization, the system comprising:
an ultrasound device comprising:
a probe configured to acquire ultrasound data for a region of interest;
a processor configured to:
compute one or more fetal measurements based on the acquired ultrasound data, wherein the one or more fetal measurements comprise an angle of progression measurement, and
generate a graphical model based at least in part on the angle of progression measurement; and
a display system configured to display the one or more computed fetal measurements and the generated graphical model.

9. The system according to claim 8, wherein the processor is configured to automatically select a pubic ramus and a fetal skull contour in the acquired ultrasound data.

10. The system according to claim 9, wherein the processor is configured to detect a tangent point where a line extending from an inferior apex of the pubic ramus intersects the fetal skull contour tangentially.

11. The system according to claim 10, wherein the processor is configured to compute the angle of progression measurement as the angle between a line drawn along the pubic ramus and the line extending from the inferior apex of the pubic ramus to the tangent point.

12. A non-transitory computer readable medium having stored thereon, a computer program having at least one code section, the at least one code section being executable by a machine for causing the machine to perform steps comprising:
computing one or more fetal measurements based on acquired ultrasound data, wherein the one or more fetal measurements comprise an angle of progression measurement;
generating a graphical model based at least in part on the angle of progression measurement; and
displaying the computed one or more fetal measurements and the generated graphical model.

13. The non-transitory computer readable medium according to claim 12, comprising automatically selecting a pubic ramus and a fetal skull contour in the acquired ultrasound data.

14. The non-transitory computer readable medium according to claim 13, comprising detecting a tangent point where a line extending from an inferior apex of the pubic ramus intersects the fetal skull contour tangentially.

15. The non-transitory computer readable medium according to claim 14, wherein the angle of progression measurement is computed as the angle between a line drawn along the pubic ramus and the line extending from the inferior apex of the pubic ramus to the tangent point.

16. The non-transitory computer readable medium according to claim 12, wherein the graphical model is a three-dimensional graphical model comprising a standard or generic fetus model positioned within a standard or generic womb model based on the angle of progression measurement.

17. The non-transitory computer readable medium according to claim 12, comprising:
applying contrast enhancement to the acquired ultrasound data to generate a contrast enhanced image; and
generating a binary representation of image pixels corresponding to a pubic ramus and a fetal skull in the contrast enhanced image by:
applying a curvature mask to the contrast enhanced image to generate a curvature mask output image,
applying a vesselness mask to the contrast enhanced image to generate a vesselness mask output image, and
combining the curvature mask output image and the vesselness mask output image.

18. The system according to claim 8, wherein the ultrasound data is acquired by transperineal ultrasound imaging.

19. The system according to claim 8, wherein the graphical model is a three-dimensional graphical model comprising a standard or generic fetus model positioned within a standard or generic womb model based on the angle of progression measurement.

20. The system according to claim 8, wherein the processor is configured to:
apply contrast enhancement to the acquired ultrasound data to generate a contrast enhanced image; and
generate a binary representation of image pixels corresponding to a pubic ramus and a fetal skull in the contrast enhanced image by:
applying a curvature mask to the contrast enhanced image to generate a curvature mask output image,
applying a vesselness mask to the contrast enhanced image to generate a vesselness mask output image, and
combining the curvature mask output image and the vesselness mask output image.

\* \* \* \* \*